(12) United States Patent
Wu et al.

(10) Patent No.: US 11,867,674 B2
(45) Date of Patent: Jan. 9, 2024

(54) GAS DETECTOR CALIBRATION CAP WITH AN EXTENDED STRIP

(71) Applicant: Honeywell International Inc., Charlotte, NC (US)

(72) Inventors: Xingguo Wu, Shanghai (CN); Yuhui Xu, Shanghai (CN); Zengping Chen, Shanghai (CN)

(73) Assignee: Honeywell International Inc., Charlotte, NC (US)

( * ) Notice: Subject to any disclaimer, the term of this patent is extended or adjusted under 35 U.S.C. 154(b) by 454 days.

(21) Appl. No.: 17/278,566

(22) PCT Filed: Oct. 2, 2018

(86) PCT No.: PCT/CN2018/109236
§ 371 (c)(1),
(2) Date: Mar. 22, 2021

(87) PCT Pub. No.: WO2020/069633
PCT Pub. Date: Apr. 9, 2020

(65) Prior Publication Data
US 2021/0356448 A1 Nov. 18, 2021

(51) Int. Cl.
*G01N 33/00* (2006.01)
(52) U.S. Cl.
CPC ..... *G01N 33/0006* (2013.01); *G01N 33/0009* (2013.01)
(58) Field of Classification Search
CPC .............. G01N 33/0006; G01N 33/0009
See application file for complete search history.

(56) References Cited

U.S. PATENT DOCUMENTS

| | | | |
|---|---|---|---|
| 6,244,093 B1 | 6/2001 | Parekh | |
| 7,275,411 B2 * | 10/2007 | Peng | .......... G01N 1/2226 73/1.06 |
| 7,281,404 B2 * | 10/2007 | Peng | .......... G01N 33/0006 73/1.06 |

(Continued)

FOREIGN PATENT DOCUMENTS

| | | |
|---|---|---|
| CN | 101228438 A | 7/2008 |
| CN | 103196522 A | 7/2013 |

(Continued)

OTHER PUBLICATIONS

European Search Report and Search Opinion received for EP Application No. 18936170.2, dated Mar. 29, 2022, 8 pages.

(Continued)

*Primary Examiner* — Nathaniel J Kolb
(74) *Attorney, Agent, or Firm* — Alston & Bird LLP

(57) ABSTRACT

Provided are methods, systems, and apparatus related to a gas detector (100, 402, 802) and a gas detector calibration cap (200, 300, 404, 703, 804). The gas detector calibration cap includes a cap body (202, 302), a first cap wing (204, 304), a second cap wing (206, 306), and an extended strip (216, 316) for opening the gas detector by inserting the extended strip in a groove (106, 707, 808) of the gas detector. The extended strip allows a worker to easily open the gas detector housing, thus improving the speed and reliability of servicing the gas detector while eliminating the potential additional cost on a separated tool for opening the gas detector housing.

20 Claims, 13 Drawing Sheets

(56) References Cited

U.S. PATENT DOCUMENTS

| | | | |
|---|---|---|---|
| 2006/0101925 A1* | 5/2006 | Peng | G01N 33/0006 73/864.41 |
| 2006/0266096 A1 | 11/2006 | Eickhoff et al. | |
| 2014/0091939 A1 | 4/2014 | Won et al. | |
| 2017/0059355 A1 | 3/2017 | Ferri et al. | |
| 2018/0172653 A1 | 6/2018 | Choi | |
| 2018/0252570 A1 | 9/2018 | Fiehn et al. | |
| 2019/0285595 A1* | 9/2019 | Lynch | G01N 33/0006 |

FOREIGN PATENT DOCUMENTS

| | | |
|---|---|---|
| CN | 204882512 U | 12/2015 |
| CN | 105699589 A | 6/2016 |
| CN | 205301290 U | 6/2016 |
| CN | 205426891 U | 8/2016 |
| CN | 205607948 U | 9/2016 |
| CN | 205982213 U | 2/2017 |
| CN | 206583890 U | 10/2017 |
| CN | 107525886 A | 12/2017 |
| CN | 206756789 U | 12/2017 |
| CN | 107850547 A | 3/2018 |
| CN | 108534872 A | 9/2018 |
| JP | 2007-248209 A | 9/2007 |
| JP | 2009281982 A | 12/2009 |
| KR | 10-2018-0001860 U | 6/2018 |
| KR | 2018-0001860 U | 6/2018 |
| KR | 20180001860 U | 6/2018 |
| TW | 201221952 A | 6/2012 |

OTHER PUBLICATIONS

CN Office Action, including Search Report, dated Oct. 31, 2022 for CN Application No. 201880097349.
Communication about intention to grant a European patent received for European Application No. 18936170.2, dated Nov. 21, 2022, 6 pages.
English Translation of CN Office Action dated Oct. 31, 2022 for CN Application No. 201880097349.
AU Notice of Allowance dated Feb. 25, 2022 for AU Application No. 2018444262, 3 pages.
Outgoing—ISA/210—International Search Report dated Jun. 28, 2019 for WO Application No. PCT/CN18/109236, 5 pages.
Outgoing Written Opinion of the ISA dated Jun. 28, 2019 for WO Application No. PCT/CN18/109236, 4 pages.
CN Notice of Allowance dated Mar. 24, 2023 for CN Application No. 201880097349, 2 page(s).
Decision to grant a European patent dated Mar. 30, 2023 for EP Application No. 18936170, 2 page(s).
English translation of CN Notice of Allowance dated Mar. 24, 2023 for CN Application No. 201880097349, 3 page(s).

* cited by examiner

GAS DETECTOR CALIBRATION CAP WITH AN EXTENDED STRIP

BACKGROUND

Applicant has identified many deficiencies and problems associated with existing methods, apparatus, and systems related to gas detector and calibration cap for the gap detector. Through applied effort, ingenuity, and innovation, many of these identified deficiencies and problems have been solved by developing solutions that are in accordance with embodiments of the present disclosure, many examples of which are described in detail herein.

BRIEF SUMMARY

The present disclosure relates generally to gas detector and gas detector calibration cap.

In accordance with various embodiments of the present invention, a gas detector calibration cap for calibrating a gas detector is provided. The gas detector calibration cap comprises a cap body, which comprises a nozzle disposed on the cap body and an exhaust opening; a first cap wing connected to the cap body, which comprises a first opening and a first overhang extending through the first opening; and a second cap wing connected to the cap body, which comprises a second opening, a second overhang extending through the second opening, and an extended strip attached to an end of the second cap wing, wherein the extended strip comprises a protrusion for opening a front shell of the gas detector.

In some embodiments, the protrusion comprises a first end and a second end, wherein the first end is attached to the extended strip, wherein a height of the first end is different than a height of the second end.

In some embodiments, the height of the second end is less than or equal to a height of a groove on an edge of the front shell of the gas detector.

In some embodiments, a width of the protrusion of the extended strip is less than or equal to a width of a groove on an edge of the front shell of the gas detector.

In some embodiments, the extended strip further comprises one or more dots disposed on a surface of the extended strip.

In some embodiments, the cap body further comprises an audio opening.

In accordance with various embodiments of the present invention, a system is provided. The system comprises a gas detector and a gas detector calibration cap. The gas detector comprises a gas detector housing and one or more sensors disposed within the gas detector housing. The gas detector housing comprises a front shell, which comprises one or more exhaust openings and a groove on an edge of the front shell; and a back shell connected to the front shell, which comprises a first slot on a first side of the back shell and a second slot on a second side of the back shell. The gas detector calibration cap comprises: a cap body, which comprises a nozzle disposed on the cap body and an exhaust opening; a first cap wing connected to the cap body, which comprises a first opening and a first overhang extending through the first opening; and a second cap wing connected to the cap body. The second cap wing comprises a second opening, a second overhang extending through the second opening; and an extended strip attached to an end of the second cap wing, wherein the extended strip comprises a protrusion for opening the front shell of the gas detector.

In some embodiments, the gas detector calibration cap is connected to the gas detector housing by securing the first overhang to the first slot and the second overhang to the second slot.

In some embodiments, the front shell of the gas detector further comprises a buzzer opening, wherein the cap body of the gas detector calibration cap further comprises an audio opening, wherein the buzzer opening overlaps the audio opening.

In some embodiments, the protrusion comprises a first end and a second end, wherein the first end is attached to the extended strip, wherein a height of the first end is different than a height of the second end.

In some embodiments, the height of the second end of the protrusion is less than or equal to a height of the groove on the edge of the front shell of the gas detector.

In some embodiments, a width of the protrusion of the extended strip is less than or equal to a width of the groove on the edge of the front shell of the gas detector.

In some embodiments, the extended strip further comprises one or more dots disposed on a surface of the extended strip.

In some embodiments, the front shell further comprises a display.

In some embodiments, the front shell further comprises one or more LED indicators.

In some embodiments, the front shell further comprises one or more buttons.

In accordance with various embodiments of the present invention, a method is provided. The method comprises inserting a protrusion of an extended strip attached to a gas detector calibration cap to a groove on an edge of a front shell of a gas detector; and applying force on the extended strip to remove the front shell from the gas detector.

In some embodiments, the method further comprises installing one or more sensors in the gas detector; and closing the gas detector by securing the front shell to a back shell of the gas detector.

In some embodiments, the method further comprises attaching the gas detector calibration cap to the gas detector.

In some embodiments, attaching the gas detector calibration cap to the gas detector further comprises securing one or more overhangs of the gas detector calibration cap to one or more slots of the gas detector.

The above summary is provided merely for purposes of summarizing some example embodiments illustrating some aspects of the present disclosure. Accordingly, it will be appreciated that the above-described embodiments are merely examples and should not be construed to narrow the scope of the disclosure in any way. It will be appreciated that the scope of the disclosure encompasses many potential embodiments in addition to those herein summarized, some of which will be further described below.

BRIEF DESCRIPTION OF THE DRAWINGS

The accompanying drawings illustrate embodiments of the disclosure, and, together with the specification, including the general description above and the detailed description which follows, serve to explain the features of the present disclosure.

DETAILED DESCRIPTION

Figure 1:
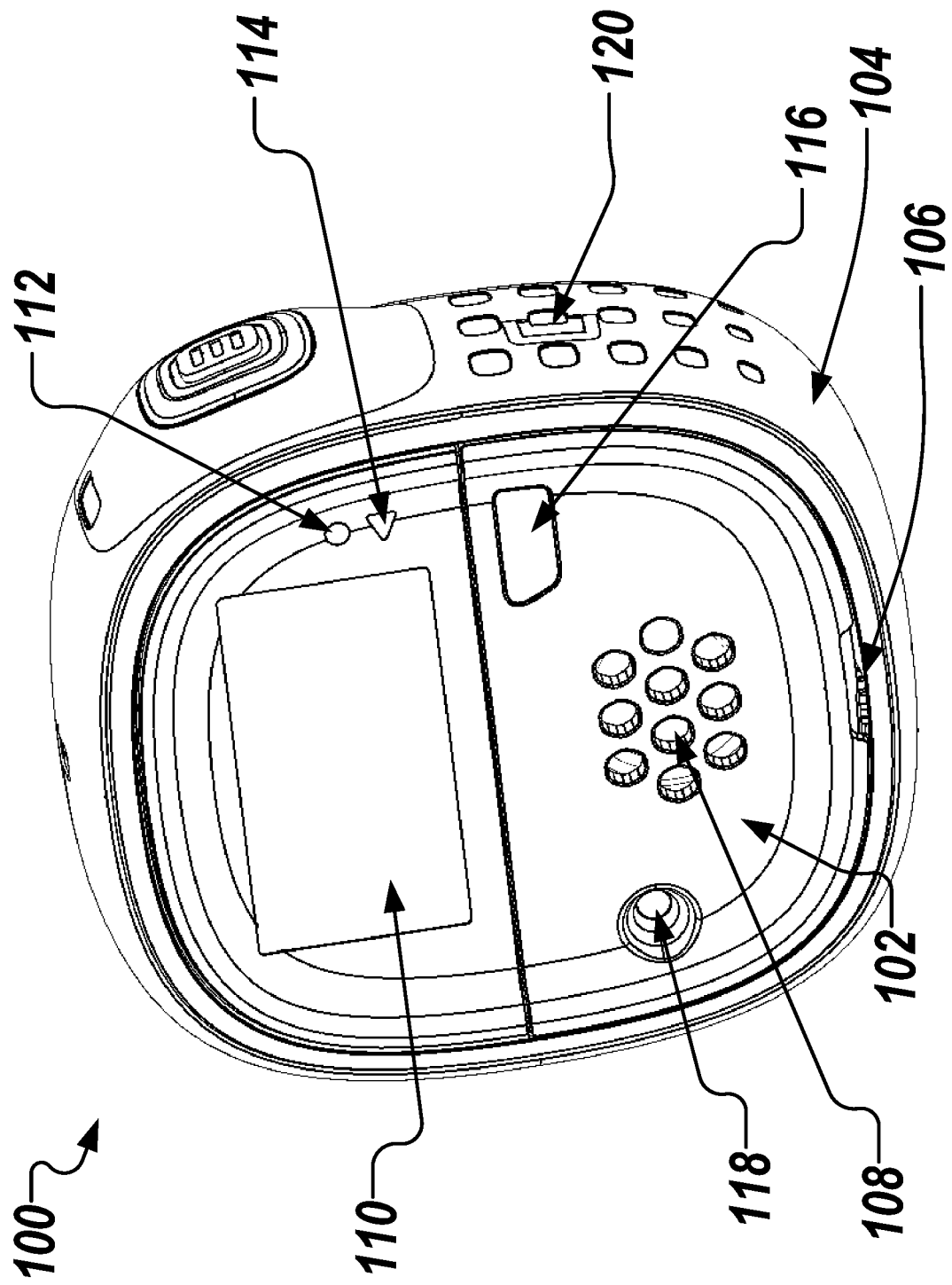
FIG. 1 illustrates an example gas detector in accordance with embodiments described herein.

The present disclosure now will be described more fully with reference to the accompanying drawings in which some but not all embodiments of the disclosure are shown. Indeed, these embodiments may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may be present in various embodiments of the disclosure described herein. In some instances, the components illustrated in the figures represent components that may not be present in various embodiments of the disclosure described herein. Accordingly, some embodiments of the present disclosure may include fewer components, more components, or different combinations of components than those shown in the figures while not departing from the scope of the disclosure.

As used herein, terms such as "front," "rear," "top," "bottom," "outside," "inside," "near," "along" and other similar terms are used for explanatory purposes in the examples provided below to describe the relative position of certain devices or portions of devices. It is noted, however, that as devices described herein, or portions thereof, may be attached or utilized in other orientations.

The term "comprising" means including but not limited to, and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," and the like generally mean that the particular feature, structure, or characteristic following the phrase may be included in at least one embodiment of the present disclosure or more than one embodiment of the present disclosure. Such phrases do not necessarily refer to the same embodiment.

The word "example" is used herein to mean "serving as an example, instance, or illustration." Any implementation described herein as "example" is not necessarily to be construed as preferred or advantageous over other implementations.

The terms "about" or "approximately" or the like, when used with a number, may mean that specific number or a range in proximity to that specific number, as understood by persons of skill in the art field.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Overview

The present invention is related generally to methods, apparatus, and systems for gas detectors. More specifically, various embodiments of the present invention describe a gas detector calibration cap with an extended strip for the gas detector.

A gas detector is a device that can detect the presence and/or concentration of various gases and vapors, such as toxic, flammable, or explosive gases, volatile organic compounds (VOCs), humidity, odors, and the like. Gas detection is important in many scenarios. For example, many workers may need to perform work in a confined space, which has limited openings for workers to enter and exit, but not designed for continuous worker occupancy. Such confined spaces may include, for example, storage tanks, ship compartments, process vessels, boilers, sewers, tunnels, and/or like. In confined space, hazardous gas can accumulate to a deadly concentration, resulting in accidents and fatalities. As such, before entering a confined space, a worker may need to test the internal atmosphere with a gas detector for oxygen content, flammable gasses and vapors, potential toxic air contaminants, and the like.

Gas detectors are generally in two forms: portable gas detector and fixed gas detector. Fixed gas detectors are permanently secured in a location, and can only detect gas within a perimeter of the location. Portable gas detectors allows a user to move the gas detector to a particular location and perform "spot reading" of that location. Portable gas detectors are essential in many areas where gas hazards could occur, because they provide continuously monitoring of an operator's breathing zone, regardless of whether the operator is stationary and moving.

However, traditional gas detectors are plagued with limitations and deficiencies. For example, gas detectors need to be routinely calibrated to ensure accurate reading, yet traditional gas detectors fail to provide means for calibration.

In addition, sensor(s) and filter(s) inside the gas detector need to be serviced and replaced for many times during product life of the gas detector. For example, continuous use of the gas detector may cause the filter to deteriorate, and therefore unable to block diffusion of gas. A sensor may have the three to five years of life, while the gas detector (for example, the casing) may have over ten years of product life. As such, the gas detector casing may need to be opened so that filters and sensors within the gas detector can be installed/replaced, yet traditional gas detectors fail to provide an easy, efficient way to open in the casing. For example, a worker may have to use a screw driver to open the gas detector casing, likely causing cracking and breaking of the gas detector casing.

Methods, apparatuses, and systems structured in accordance with various embodiments of the invention provide specific, technical solutions to these technical problems faced by traditional gas detectors. For example, various embodiments of the invention implement a gas detector calibration cap, which provides means for performing accurate calibration of the gas detector. In addition, the gas detector calibration cap includes an extended strip, allowing a worker to easily open the gas detector housing. In other words, the present invention provides means for opening the gas detector housing without breaking the gas detector housing, while integrating such means into the gas detector calibration cap. As a result, the present invention improves the speed and reliability of servicing the gas detector, while eliminating the potential additional cost on special and separate tooling for opening the gas detector housing.

As such, various embodiments of the present invention overcome challenges faced by traditional gas detectors, details of which are described hereinafter.

Example Apparatus for Implementing Embodiments of the Present Invention

As should be appreciated, various embodiments of the present invention may be implemented as apparatus, systems, and/or the like. For example, embodiments of the present invention include a gas detector and a gas detector calibration cap for calibrating the gas detector.

1. Gas Detector

Referring now to FIG. 1, an example gas detector 100 is shown. The gas detector 100 comprises a gas detector housing and one or more sensors or filters disposed within the gas detector housing.

The gas detector housing is formed by a front shell 102 and a back shell 104. The front shell 102 and the back shell 104 may be secured together through snap-fit mechanisms. In some embodiments, the front shell 102 may comprise flexible member (such as cantilever) extending from the bottom surface around the edge, and the back shell 104 may comprise grooves around its periphery that provide space for the flexible member. In some embodiments, other snap-fit mechanisms may be used, without departing from the scope of the present disclosure.

As shown in FIG. 1, the front shell 102 further comprises a groove 106 on the edge of the front shell 102. The groove 106 provides mean for disconnecting the front shell 102 from the back shell 104, details of which are described hereinafter.

As shown in FIG. 1, the front shell further comprises one or more exhaust openings 108. The one or more exhaust openings 108 allow the gas to pass through the front shell 102 and to/from inside the gas detector housing, where the one or more sensors are disposed. The gas sensors may include sensors that can detect the presence and concentration of gas such as CO, $H_2S$, $O_2$, $CL_2$, $H_2$, CO—H, $SO_2$, HCN, $O_3$, $PH_3$, $NO_2$, NO, $CLO_2$, $NH_3$, and the like.

The front shell may further comprise one or more displays. For example, as shown in FIG. 1, the front shell 102 comprises a LED display 110. The LED display presents information, such as operation menu of the gas detector 100, instructions for operating the gas detector 100, results of gas detections (for example, type of the gas, concentration of the gas, etc.), and the like.

The front shell may further comprise one or more indicators. For example, as shown in FIG. 1, the front shell 102 comprises LED indicators 112 and 114. The LED indicators 112 and 114 provide indications regarding sensor readings. For example, when the LED indicator 112 is flashing red, it may indicate that the concentration of certain gas exceeds a threshold. When the LED indicator 114 stays on green, it may indicate that the gas detector 100 is in the process of detecting gas.

The front shell 102 may further comprise input means, such as one or more buttons, touch sensors, touch bottoms, or the like. For example, as shown in FIG. 1, the front shell 102 comprises a touch button 116. The touch bottom 116 allows a user to, for example, provide input to select an item from the operation menu displayed on the LED display 110.

In some embodiments, the gas detector may further comprise a infrared (IR) sensor (for example, a passive infrared sensor) for receiving and/or measuring IR light signals.

The front shell 102 may further comprise a buzzer aperture 118, allowing sound to be transmitted from within the gas detector housing (for example, from a buzzer). In some embodiments, when the gas detector 100 determines that certain gas exceeds a threshold, the buzzer may emit warning sound through the buzzer aperture 118 to provide warning for hazardous environment.

The back shell 104 may comprise a slot on each side. For example, FIG. 1 illustrates a slot 120 on one side of the back shell 104. The slot 120 provides fastening mechanisms for attaching a gas detector calibration cap to the gas detector, details of which are described hereinafter.

In some embodiment, the front shell 102 may comprise two detachable portions: a top portion and a bottom portion. In this regard, the display 110 and LED indicators 112 and 114 may be on the top portion. The buzzer aperture 118, exhaust openings 108, and the groove 106 may be on the bottom portion. Additionally, the back shell 104 may comprise two corresponding detachable portions: a top portion securing the top portion of the front shell 102 and a bottom portion securing the bottom portion of the front shell 102.

In various embodiments, one or more other components may be disposed within the gas detector housing. For example, one or more processors may be in communication with the one or more sensors described above to determine the presence and/or concentration of gas. The one or more processors may include a single core processor, a multi-core processor, and/or the like. The one or more processors may further be in communication with one or more non-transitory storage medium, including, for example, volatile memories, non-volatile memories, and the like. The one or more non-transitory storage medium may be configured to store information, data, content, applications, instructions, or the like for enabling the one or more processors to carry out various functions, such as determining the presence of gas and calculating the concentration of gas.

2. Gas Detector Calibration Cap

Figure 2:
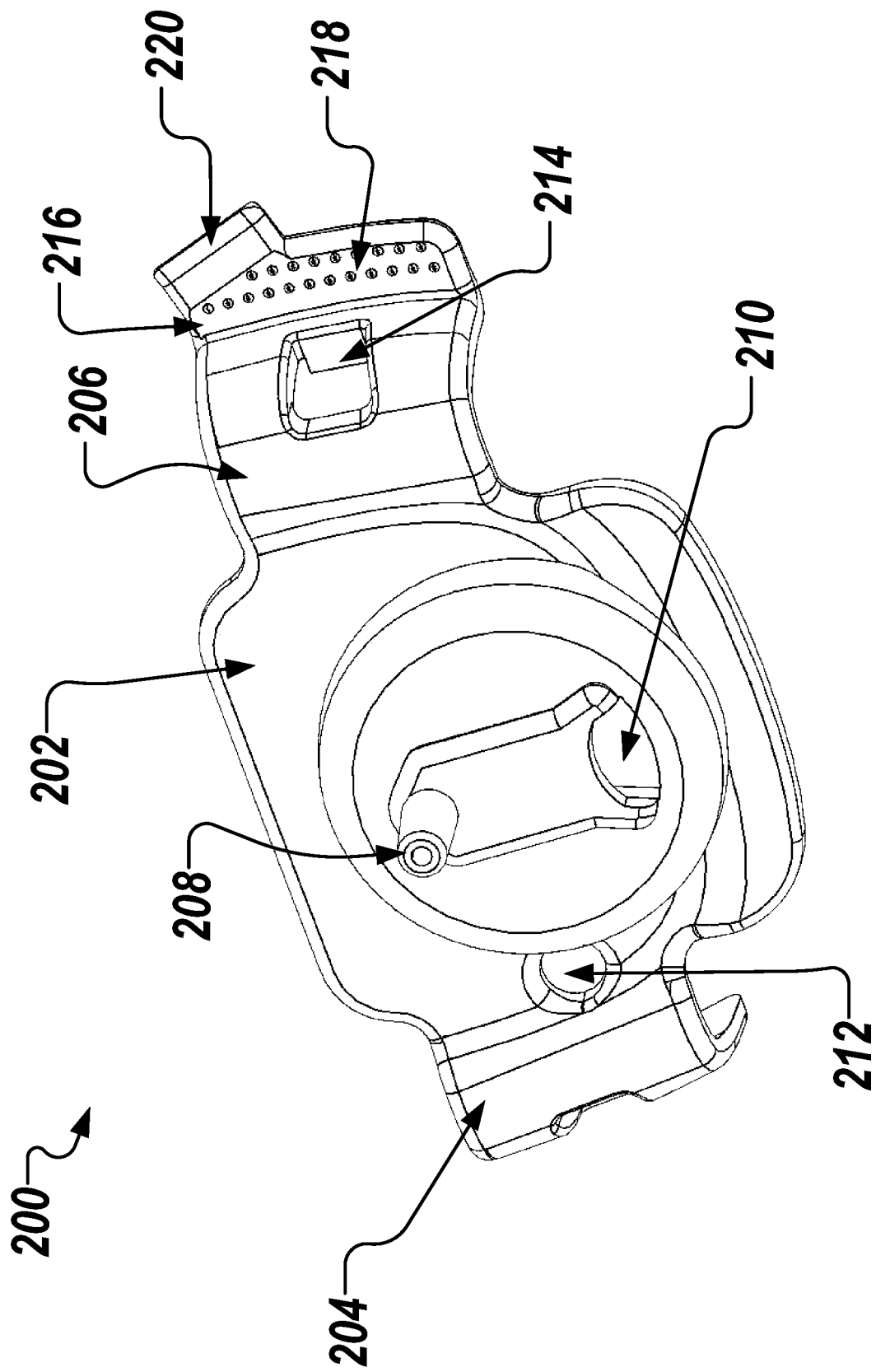
FIG. 2 illustrates an example gas detector calibration cap in accordance with embodiments described herein.

Referring now to FIG. 2, an example gas detector calibration cap 200 is shown. The gas detector calibration cap 200 includes a cap body 202, a first cap wing 204 and a second cap wing 206.

The cap body may comprise one or more nozzles. For example, as shown in FIG. 2, a nozzle 208 is disposed on the cap body 202. During calibration, the nozzle 208 allows calibration gas (i.e. gas with known concentration) to flow into the gas detector, so that the gas detector can reestablish baselines for sensors.

The cap body may further comprise one or more exhaust openings. For example, as shown in FIG. 2, the cap body 202 comprises an exhaust opening 210. The exhaust openings allows the calibration gas to leave the gas detector.

The cap body 202 may further comprise one or more audio openings. For example, as shown in FIG. 2 the cap body 202 includes an audio aperture 212. The audio aperture 212 corresponds to the buzzer aperture of the gas detector, allowing sound to be transmitted from within the gas detector to the outside.

Each of the first cap wing 204 and the second cap wing 206 may comprise an opening and an overhang extending through the opening. For example, as shown in FIG. 2, the second cap wing 206 comprise overhang 214 extending thought the opening. The overhang in each cap wing provides means for securing the gas detector calibration cap 200 to a gas detector, details of which are described hereinafter.

As shown in FIG. 2, the second cap wing 206 further comprise an extended strip 216 extending from the end of the second cap wing 206. The extended strip 216 may further include a protrusion 220. The protrusion 220 may further comprise a first end and a second end, where the first end is opposite to the second end. The first end may be attached to the extended strip 216, while the second end has a height different than the height of the first end.

As described further in details below, the protrusion 220 can be used to open the font shell of the gas detector. In this regard, the height of the second end may be equal to or less than the height of the groove on the edge of the front shell of the gas detector. The width of the second end may be equal to or less than the width of the groove on the edge of the front shell of the gas detector.

In some embodiments, the extended strip of the gas detector calibration cap may include one or more dots. For example, as shown in FIG. 2, the extended strip 216 includes dots 218. The dots 218 are protrusions from the surface of the extended strip 216. When a user applies force on the extended strip 216 using, for example, a finger, the dots 218 prevent the finger from slipping off the extended strip 216.

Figure 3A:
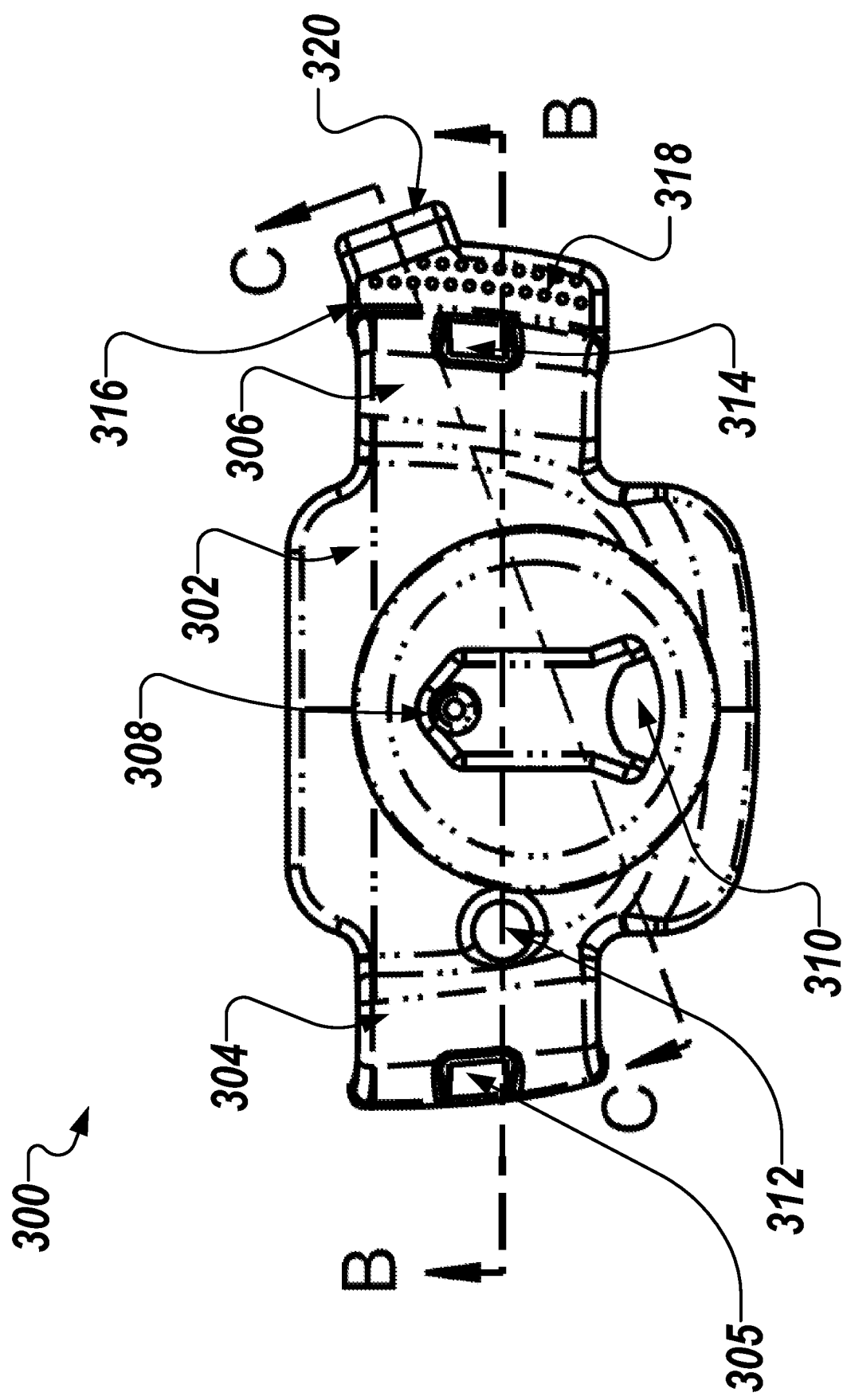
FIGS. 3A, 3B, 3C, 3D, and 3E illustrate various views of an example gas detector calibration cap in accordance with embodiments described herein.
Figure 3B:
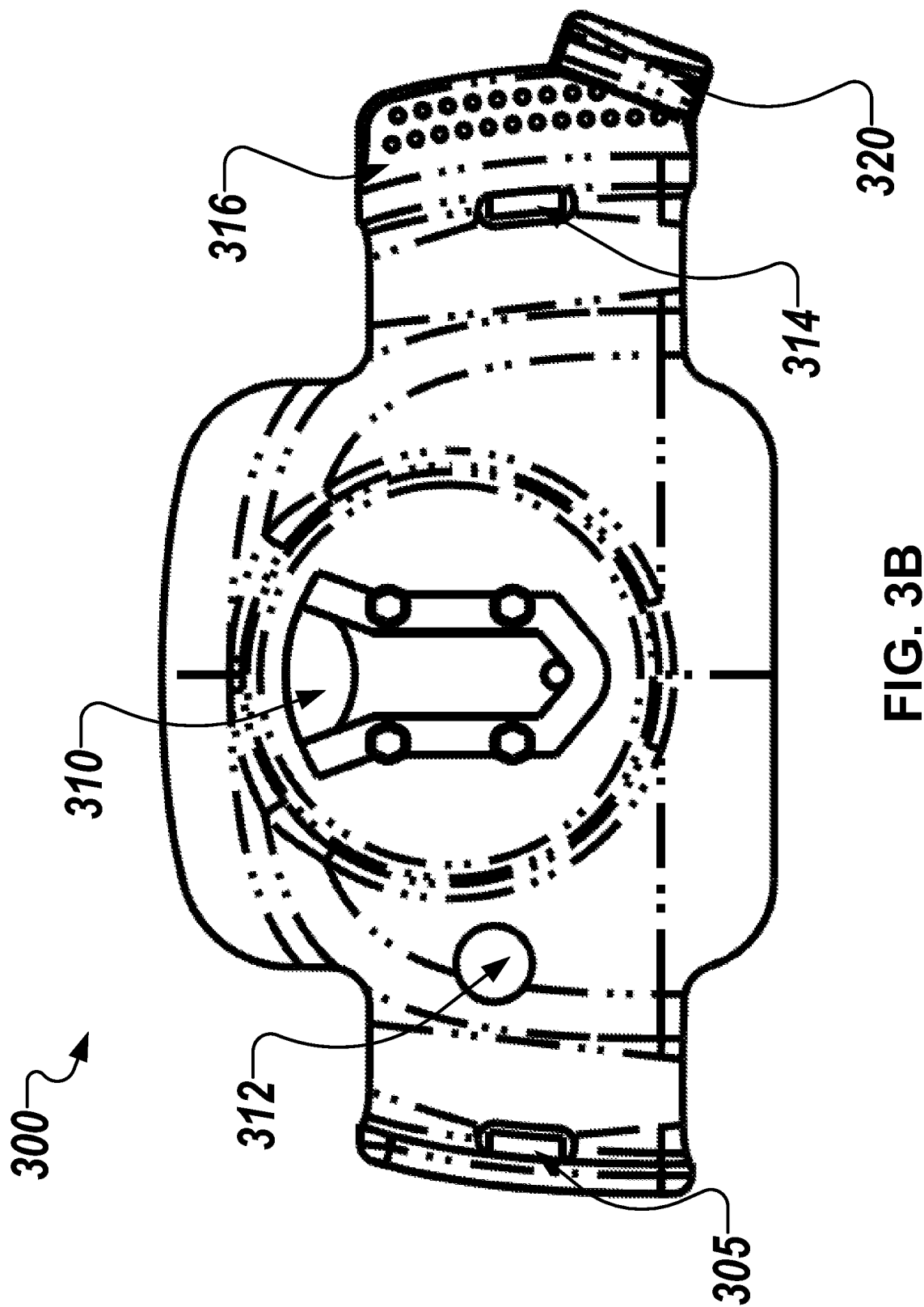

FIG. 3A-3E illustrate various views of an example gas detector calibration cap 300. Referring now to FIGS. 3A and 3B, FIG. 3A provides a top view of the gas detector calibration cap 300, and FIG. 3B provides a bottom view of the gas detector calibration cap 300.

As shown in FIGS. 3A-3B, the gas detector calibration cap 300 may include a cap body 302, a first cap wing 304, and a second cap wing 306, similar to the cap body 202, the first cap wing 204, and the second cap wing 206 described above with reference to FIG. 2, respectively. The cap body 302 may include a nozzle 308, an audio aperture 312, and an exhaust opening 310, similar to the nozzle 208, the audio aperture 212, and the exhaust opening 210 as described above with reference to FIG. 2.

The first cap wing 304 may include a first overhang 305 extending through a first opening, and the second cap wing 306 may include a second overhang 314 extending through a second opening. The first overhang 305 and the second overhang 314 allow the gas detector calibration cap 300 to be securely attached to the gas detector, details of which are described hereinafter.

Further, the second cap wing 306 includes an extended strip 316, similar to the extended strip 216 described above with reference to FIG. 2. The extended strip 316 may include an protrusion 320, similar to the protrusion 220 described above with reference to FIG. 2. The extended strip 316 may further include dots 318, similar to dots 218 described above with reference to FIG. 2.

Figure 3C:
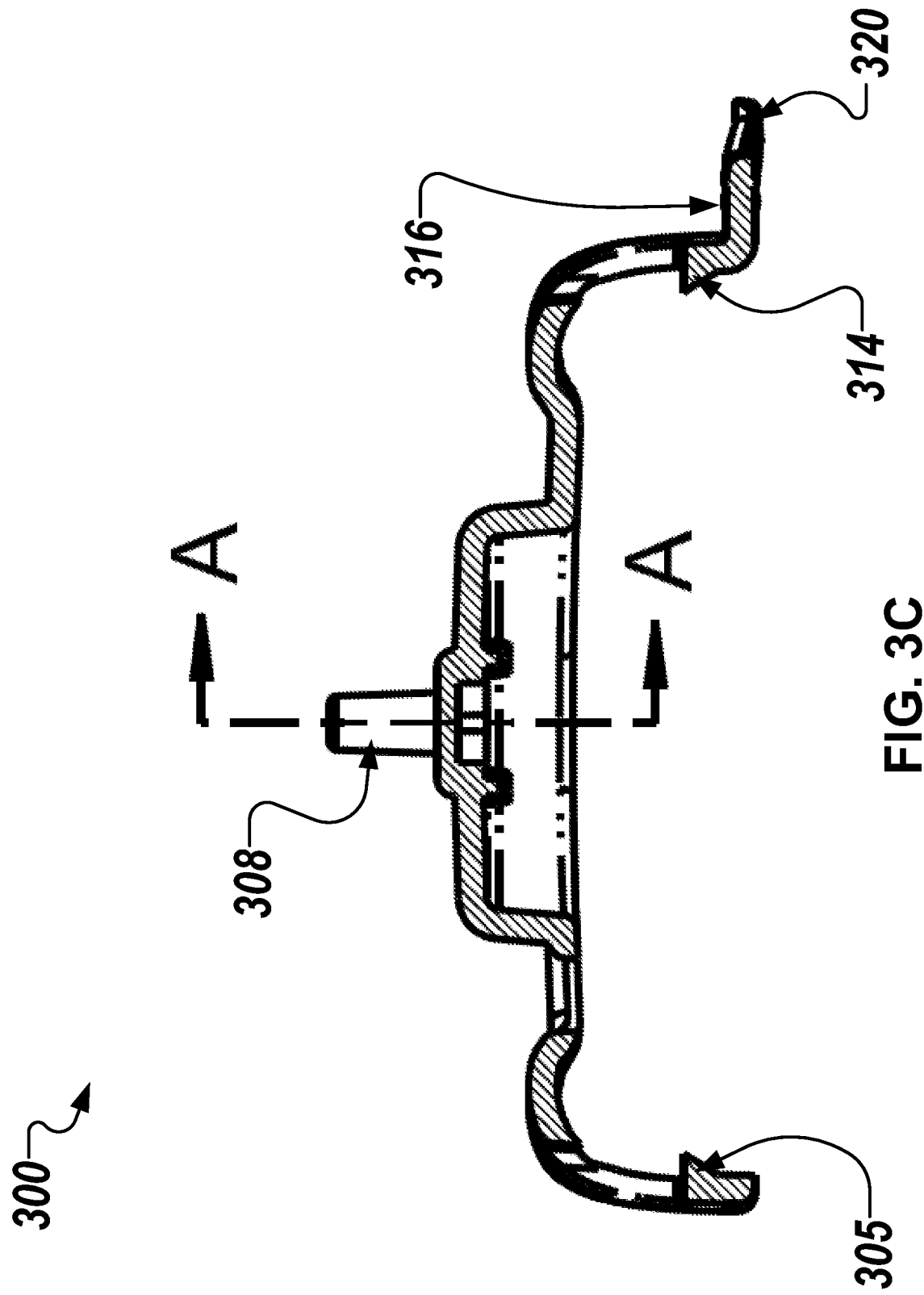

Referring to FIG. 3C, a cross-section view of the gas detector calibration cap 300 from the B-B cut line of FIG. 3A is shown. FIG. 3C illustrates various components of the gas detector calibration cap 300, including, for example, the nozzle 308, the first overhang 305, the second overhang 314, the extended strip 316 and the protrusion 320.

Figure 3D:
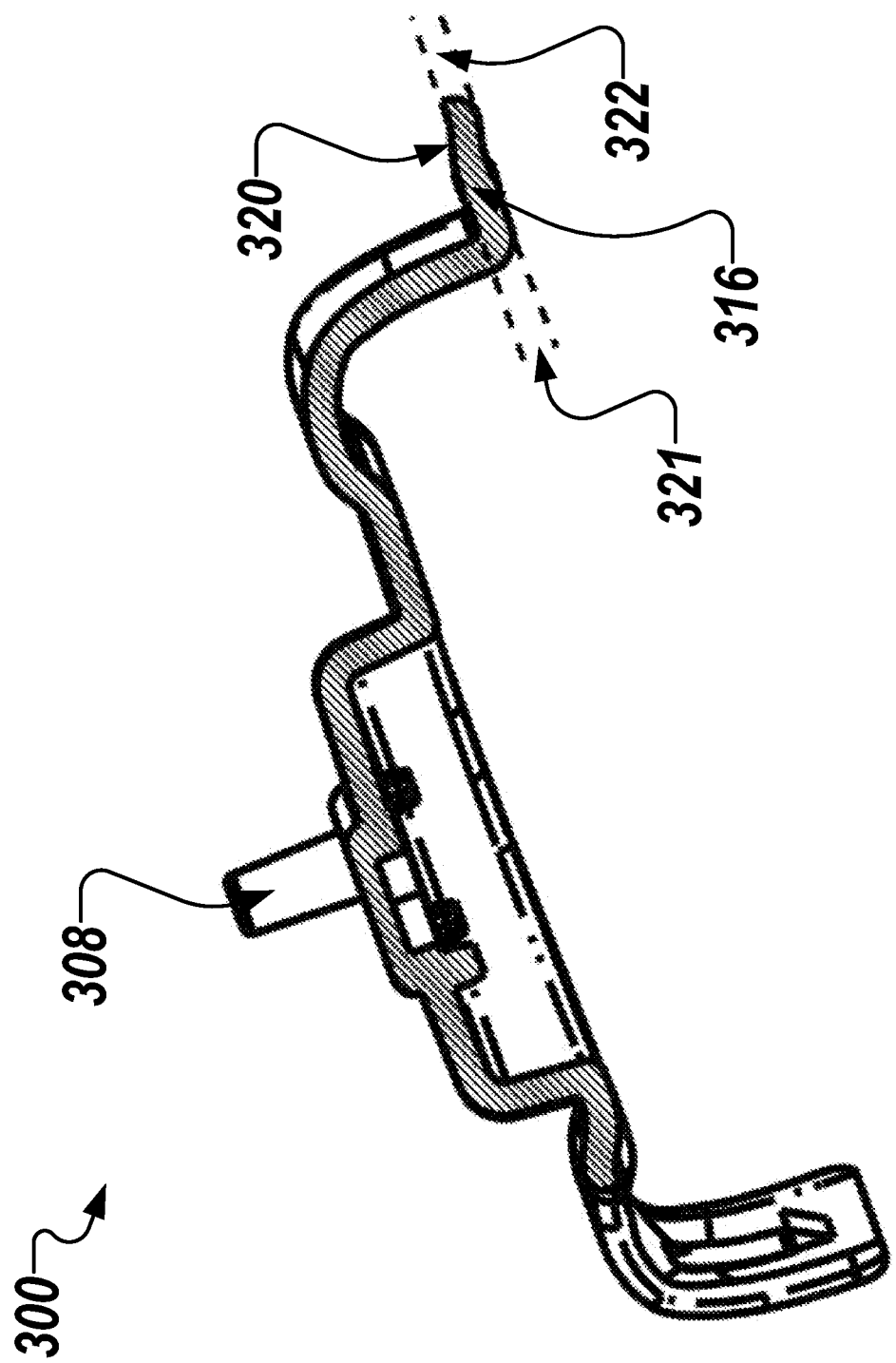

Referring to FIG. 3D, a cross-section view of the gas detector calibration cap 300 from the A-A cut line of FIG. 3B is shown. FIG. 3D illustrates various components of the gas detector calibration cap 300, including, for example, the nozzle 308, the extended strip 316, and the protrusion 320. As shown in FIG. 3D, the protrusion 320 may be curved. The protrusion 320 has a first end and second end, with the first end attached to the extended strip 316. The height 321 of the first end is different than the height 322 of the second end. For example, the height 322 may be less than or equal to the height of groove on the front shell of the gas detector so that the protrusion 320 can be inserted into the groove.

Figure 3E:
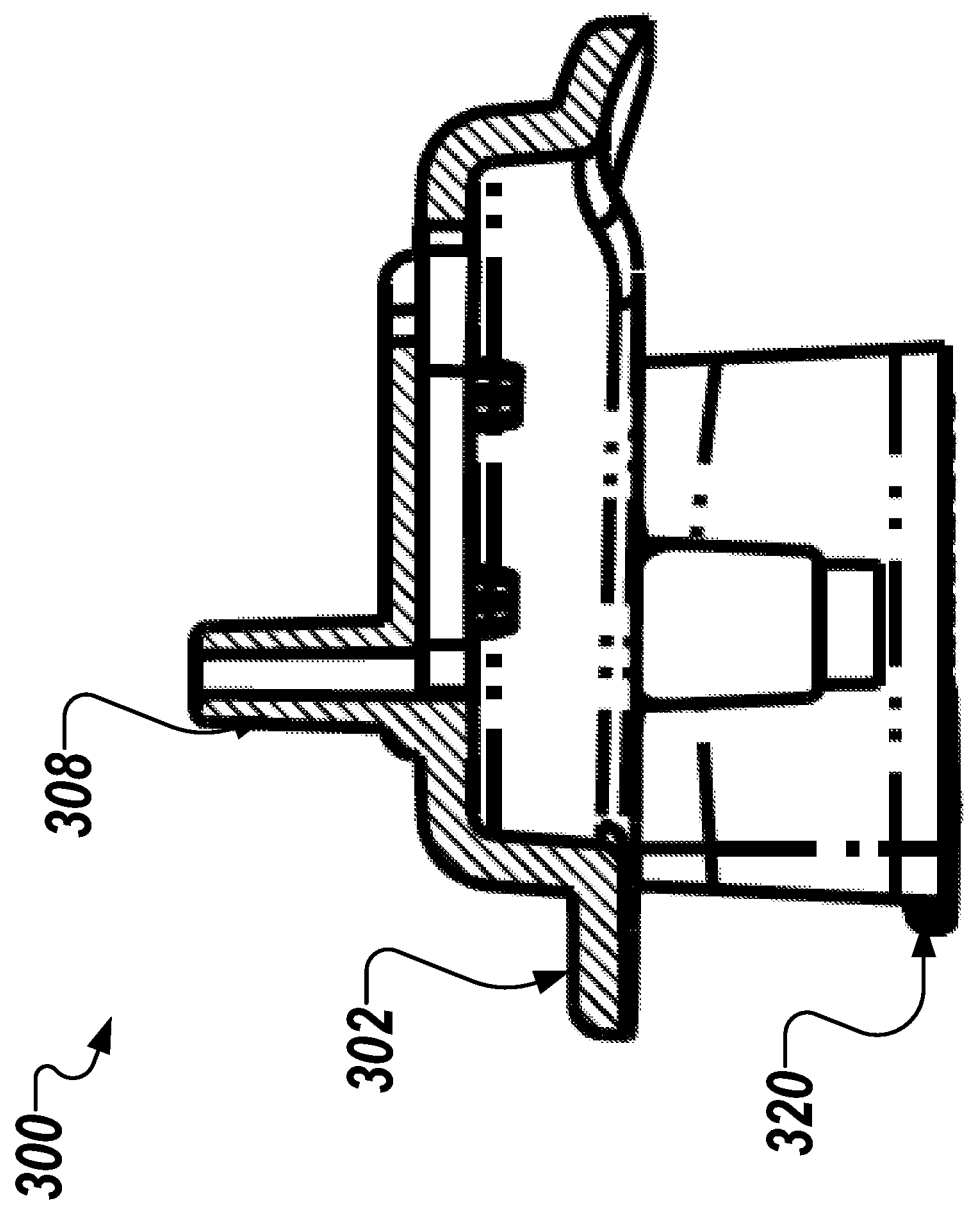

Referring to FIG. 3E, a cross-section view of the gas detector calibration cap 300 from the C-C cut line of FIG. 3A is shown. FIG. 3E illustrates various components of the gas detector calibration cap 300, including, for example, the nozzle 308, the cap body 302, and the protrusion 320.

Example System for Implementing Embodiments of the Present Invention

Figure 4:
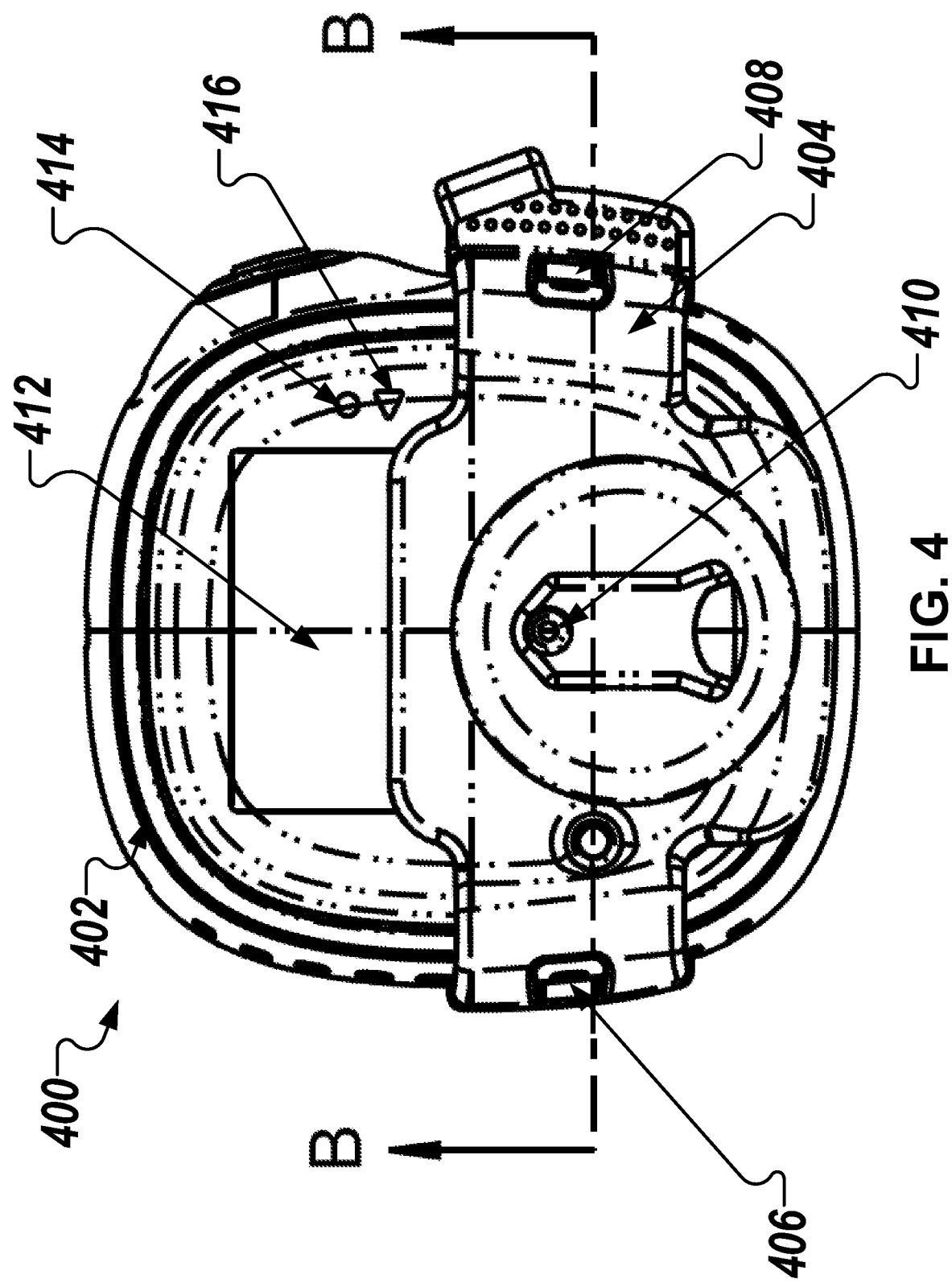
FIG. 4 illustrates an example system for calibrating a gas detector in accordance with embodiments described herein.

In accordance with various embodiments of the present invention, a system for calibrating a gas detector is provided. For example, as shown in FIG. 4, the system 400 comprises a gas detector 402 and a gas detector calibration cap 404. The gas detector may be, for example, the gas detector 100 described above with reference to FIG. 1. The gas detector calibration cap 404 may be, for example, the gas detector calibration cap 200 described above with reference to FIG. 2, and the gas detector calibration cap 300 described above with reference to FIGS. 3A-3E.

As shown in FIG. 4, the gas detector calibration cap 404 is secured to the gas detector 402 using overhangs 406 and 408. During calibration, the calibration gas flows through the nozzle 410 to the gas detector 402. The display 412 of the gas detector 402 may display instructions on when to start the gas flow and when to stop the gas flow. The LED indicator lights 414 and 416 may indicate the status of calibration.

Figure 5:
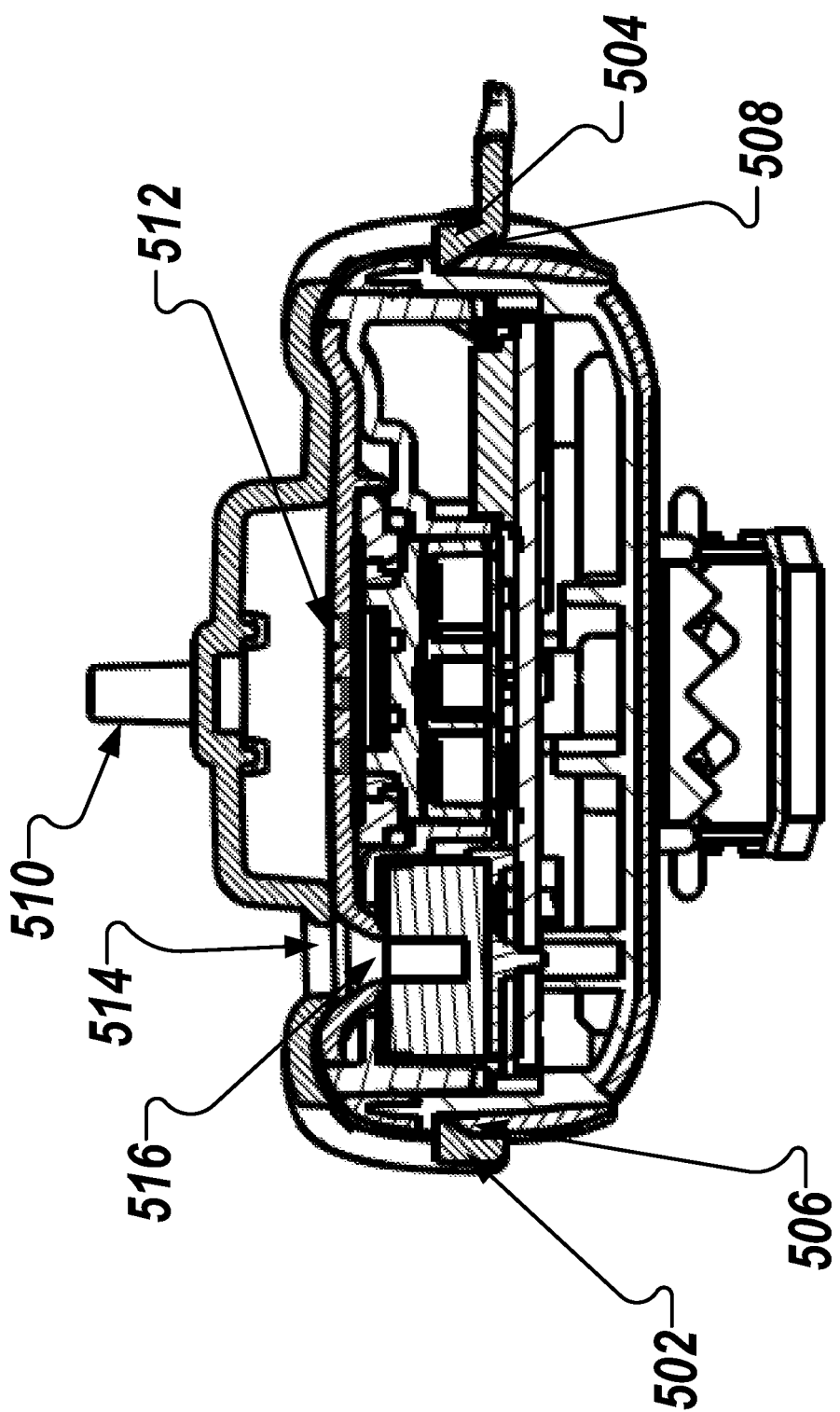
FIG. 5 illustrates a cross-section view of an example system for calibrating a gas detector.

Referring now to FIG. 5, a cross-section view of the system from the cut line B-B of FIG. 4 is shown. As shown in FIG. 5, the overhangs 502 and 504 of the gas detector calibration cap are secured to the slots 506 and 508 of the gas detector, respectively, thereby securing the gas detector calibration cap to the gas detector. The nozzle 510 of the gas detector calibration cap allows the calibration gas to flow to the sensors through the exhaust openings 512 of the gas detector. The audio aperture 514 of the gas detector calibration cap overlaps the buzzer aperture 516 of the gas detector, such that buzzer sound can be transmitted from inside the gas detector to the outside.

Figure 6:
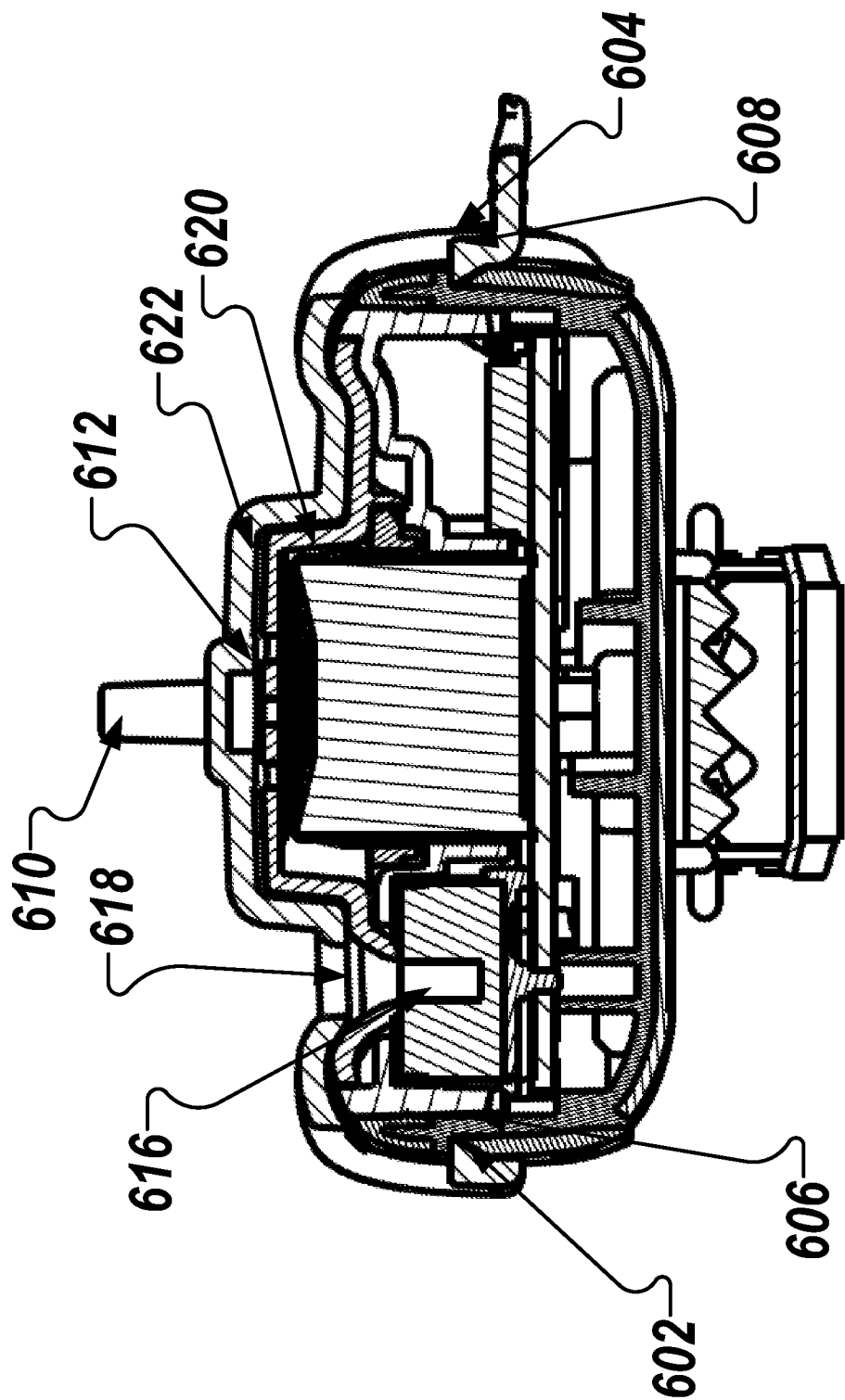
FIG. 6 illustrates a cross-section view of an example system for calibrating a gas detector.

Referring now to FIG. 6, another cross-section view of the system from the cut line B-B of FIG. 4 is shown. Similar to those described above with reference to FIG. 5, the overhangs 602 and 604 of the gas detector calibration cap are secured to the slots 606 and 608 of the gas detector, respectively, thereby securing the gas detector calibration cap to the gas detector. The audio aperture 618 of the gas detector calibration cap overlaps the buzzer aperture 616 of the gas detector, such that buzzer sound can be transmitted from inside the gas detector to the outside.

Further, as shown in FIG. 6, the gas detector may comprise a protruded portion 620, where the exhaust openings 612 are on top of the protruded portion 620. In this regard, the gas detector calibration cap comprises a corresponding protruded portion 622, allowing the protruded portion 622 to house the protruded portion 620. As such, the calibration gas flows through the nozzle 610 of the gas detector calibration cap to the sensors in the gas detector through the exhaust openings 612.

Example Method for Implementing Embodiments of the Present Invention

As described above, various embodiments of the present invention may be implemented as methods. For example, embodiments of the present invention include a method for removing the front shell of a gas detector form the gas detector housing.

Figure 7:
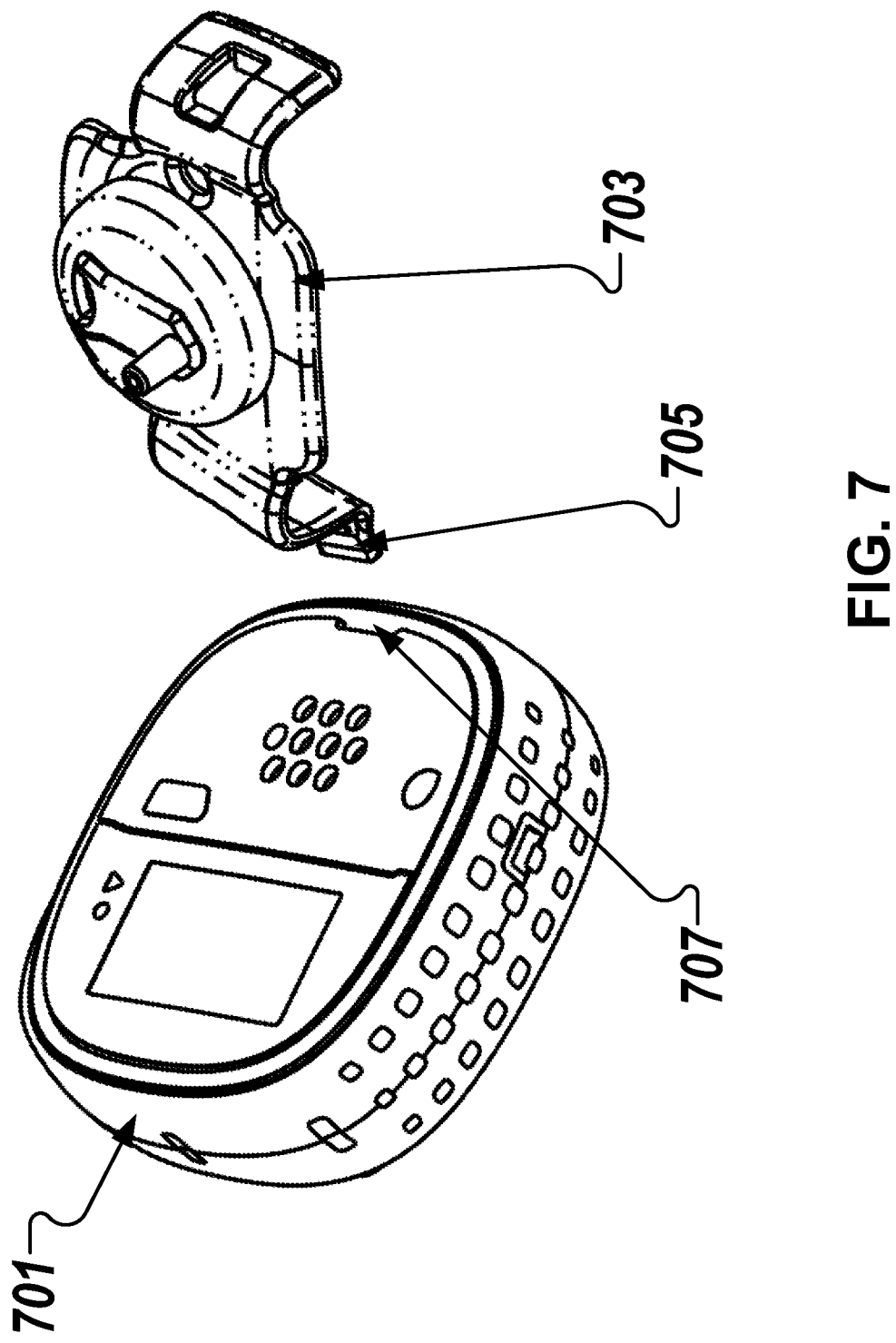
FIG. 7 illustrates an example method of operating an example gas detector and an example gas detector calibration cap in accordance with embodiments described herein.

Referring now to FIG. 7, a gas detector 701 and a gas detector calibration cap 703 are shown. The gas detector 701 may be, for example, the gas detector 100 described above with reference to FIG. 1. For example, the gas detector 701 comprises a groove 707, similar to the groove 106 described above in reference to FIG. 1.

The gas detector calibration cap 703 may be, for example, the gas detector calibration cap 200 described above with reference to FIG. 2 and the gas detector calibration cap 300 described above with reference to FIGS. 3A-3E. For example, the gas detector calibration cap 703 comprises a protrusion 705 from an extended strip, similar to the protrusion 220 described above with reference to FIG. 2 and protrusion 320 described above with reference to FIGS. 3A-3E.

Figure 8A:
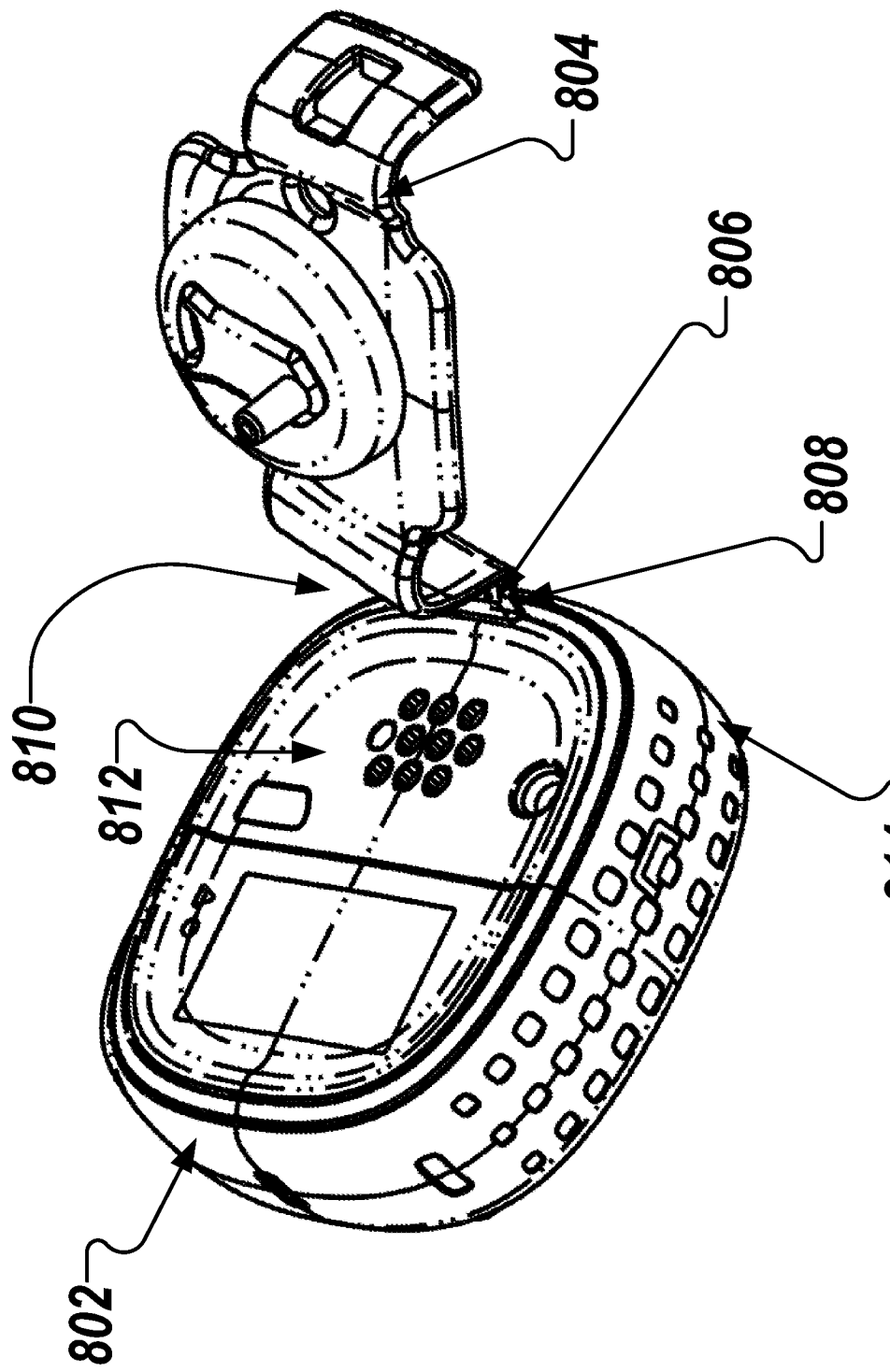
FIGS. 8A-8B illustrate various views of an example gas detector and an example gas detector calibration cap in an example method.
Figure 8B:
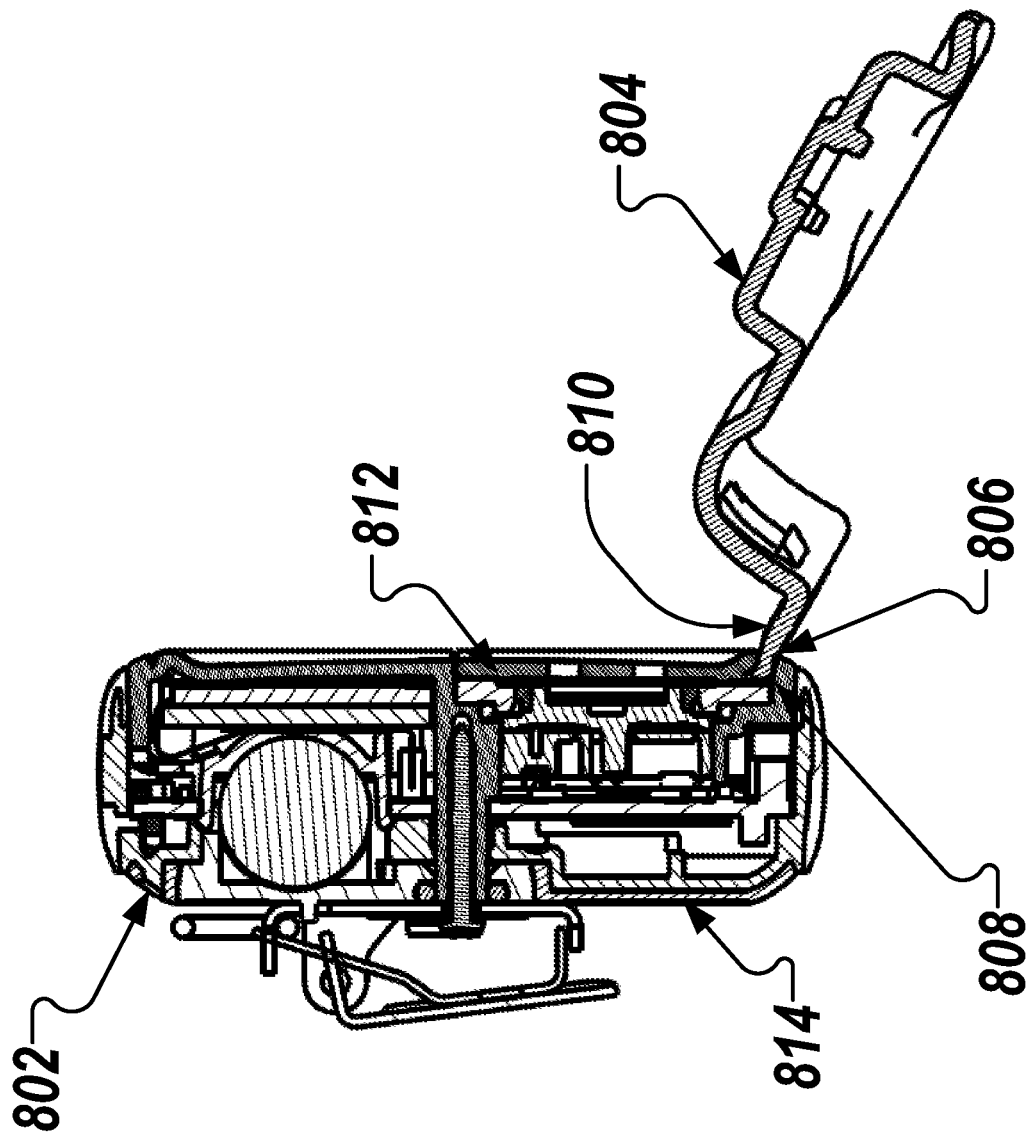

Referring now to FIGS. 8A-8B, a user may remove the front shell of the gas detector by inserting the protrusion of the extended strip attached to the gas detector calibration cap to the groove on the edge of the front shell of the gas detector, and applying force on the extended strip.

For example, FIG. 8A illustrates inserting the protrusion 806 of the gas detector calibration cap 804 to the groove 808 of the gas detector 802, and applying force in the direction of 810 on the extended strip to cause the front shell 812 of the gas detector 802 to be dis-attached from the back shell 814.

FIG. 8B is a cross-section view of FIG. 8A. As shown in FIG. 8B, the protrusion 806 of the gas detector calibration cap 804 is aligned with the groove 808, and is inserted into the groove 808 of the gas detector 802. After inserting the protrusion 806, a user may apply force in the direction of 810, causing the front shell 812 to be dis-attached from the back shell 814.

As described above, the front shell of the gas detector may comprise a top portion and a bottom portion. In these embodiments, when force is applied to the extended strip, only the bottom portion is removed from the gas detector housing.

In various embodiments of the present invention, after the font shell is remove from the back shell, a user may install and/or replace one or more sensor(s) and/or filter(s) installed within the gas detector. The user may close the gas detector housing by securing the front shell to the back shell, such as through the snap-fit mechanisms described above.

In various embodiments of the present invention, the user may further attach the gas detector calibration cap to the gas detector after the front shell is attached to the back shell. In this regard, the user may secure the gas detector calibration cap to the gas detector using overhangs from the gas detector calibration cap and slots from the gas detector, similar to those described above.

Additional Implementation Details

Furthermore, any advantages and features described above may relate to specific embodiments, but shall not limit the application of such issued claims to processes and structures accomplishing any or all of the above advantages or having any or all of the above features.

In addition, the section headings used herein are provided for consistency with the suggestions under applicable law, rules, and/or regulations or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, that are protected thereby. In all instances, the scope of the claims shall be considered on their own merits in light of this disclosure, but should not be constrained by the headings set forth herein.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatus and systems described herein, it is understood that various other components may be used in conjunction. Therefore, it is to be understood that the disclosure is not to be limited to the specific embodiments disclosed and that modifications and other embodiments are intended to be included within the scope of the appended claims. For example, the various elements or components may be combined or integrated in another system or certain features may be omitted or not implemented. Moreover, the steps in any method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

The invention claimed is:

1. A gas detector calibration cap for calibrating a gas detector, the gas detector calibration cap comprising:
   a cap body, comprising a nozzle disposed on the cap body and an exhaust opening;
   a first cap wing connected to the cap body, comprising a first opening and a first overhang extending through the first opening;
   a second cap wing connected to the cap body, comprising:
      a second opening;
      a second overhang extending through the second opening; and
      an extended strip attached to an end of the second cap wing, wherein the extended strip comprises a protrusion for opening a front shell of the gas detector.

2. The gas detector calibration cap according to claim 1, wherein the protrusion comprises a first end and a second end, wherein the first end is attached to the extended strip, wherein a height of the first end is different than a height of the second end.

3. The gas detector calibration cap according to claim 2, wherein the height of the second end is less than or equal to a height of a groove on an edge of the front shell of the gas detector.

4. The gas detector calibration cap according to claim 1, wherein a width of the protrusion of the extended strip is less than or equal to a width of a groove on an edge of the front shell of the gas detector.

5. The gas detector calibration cap according to claim 1, wherein the extended strip further comprises one or more dots disposed on a surface of the extended strip.

6. The gas detector calibration cap according to claim 1, wherein the cap body further comprises an audio opening.

7. A system comprising a gas detector and a gas detector calibration cap, wherein the gas detector comprises:
a gas detector housing, comprising:
a front shell, comprising
one or more exhaust openings; and
a groove on an edge of the front shell;
a back shell connected to the front shell, comprising
a first slot on a first side of the back shell;
a second slot on a second side of the back shell; and
one or more sensors disposed within the gas detector housing; and
wherein the gas detector calibration cap comprises:
a cap body, comprising a nozzle disposed on the cap body and an exhaust opening;
a first cap wing connected to the cap body, comprising a first opening and a first overhang extending through the first opening; and
a second cap wing connected to the cap body, comprising:
a second opening;
a second overhang extending through the second opening; and
an extended strip attached to an end of the second cap wing, wherein the extended strip comprises a protrusion for opening the front shell of the gas detector.

8. The system according to claim 7, wherein the gas detector calibration cap is connected to the gas detector housing by securing the first overhang to the first slot and the second overhang to the second slot.

9. The system according to claim 7, wherein the front shell of the gas detector further comprises a buzzer opening, wherein the cap body of the gas detector calibration cap further comprises an audio opening, wherein the buzzer opening overlaps the audio opening.

10. The system according to claim 7, wherein the protrusion comprises a first end and a second end, wherein the first end is attached to the extended strip, wherein a height of the first end is different than a height of the second end.

11. The system according to claim 10, wherein the height of the second end of the protrusion is less than or equal to a height of the groove on the edge of the front shell of the gas detector.

12. The system according to claim 11, wherein a width of the protrusion of the extended strip is less than or equal to a width of the groove on the edge of the front shell of the gas detector.

13. The system according to claim 7, wherein the extended strip further comprises one or more dots disposed on a surface of the extended strip.

14. The system according to claim 7, wherein the front shell further comprises a display.

15. The system according to claim 7, wherein the front shell further comprises one or more LED indicators.

16. The system according to claim 7, wherein the front shell further comprises one or more buttons.

17. A method, comprising:
inserting a protrusion of an extended strip attached to a gas detector calibration cap to a groove on an edge of a front shell of a gas detector; and
applying force on the extended strip to remove the front shell from the gas detector.

18. The method according to claim 17, further comprising:
installing one or more sensors in the gas detector; and
closing the gas detector by securing the front shell to a back shell of the gas detector.

19. The method according to claim 18, further comprising attaching the gas detector calibration cap to the gas detector.

20. The method according to claim 19, wherein attaching the gas detector calibration cap to the gas detector further comprises securing one or more overhangs of the gas detector calibration cap to one or more slots of the gas detector.

* * * * *